US012738345B2

(12) United States Patent
Van 'T Oever

(10) Patent No.: US 12,738,345 B2
(45) Date of Patent: Sep. 15, 2026

(54) METHOD FOR PROVIDING A DETECTION OUPUT WHICH IS REPRESENTATIVE FOR THE PRESENCE OF A MOLECULE OF INTEREST

(71) Applicant: MICRONIT HOLDING B.V., Enschede (NL)

(72) Inventor: Ronny Van 'T Oever, Epse (NL)

(73) Assignee: MICRONIT HOLDING B.V., Enschede (NL)

( * ) Notice: Subject to any disclaimer, the term of this patent is extended or adjusted under 35 U.S.C. 154(b) by 406 days.

(21) Appl. No.: 18/554,299

(22) PCT Filed: Apr. 16, 2022

(86) PCT No.: PCT/NL2022/050211
§ 371 (c)(1),
(2) Date: Oct. 6, 2023

(87) PCT Pub. No.: WO2022/220686
PCT Pub. Date: Oct. 20, 2022

(65) Prior Publication Data

US 2024/0290432 A1 Aug. 29, 2024

(30) Foreign Application Priority Data

Apr. 16, 2021 (NL) ..................................... 2028003

(51) Int. Cl.
*G16B 40/10* (2019.01)
*C12Q 1/6851* (2018.01)
(Continued)

(52) U.S. Cl.
CPC ........... *G16B 40/10* (2019.02); *C12Q 1/6851* (2013.01); *G06V 20/698* (2022.01); *G16B 25/00* (2019.02)

(58) Field of Classification Search
None
See application file for complete search history.

(56) References Cited

U.S. PATENT DOCUMENTS 6,783,934 B1 * 8/2004 McMillan ............ G01N 21/278 536/25.32
7,469,186 B2 * 12/2008 Taylor, Jr. ............ C12Q 1/6851 702/19

(Continued)

FOREIGN PATENT DOCUMENTS

AU 2011272868 A1 * 2/2013 ........... C12Q 1/6816
AU 2011272868 B2 * 9/2015 ........... C12Q 1/6844

(Continued)

OTHER PUBLICATIONS

International Search Report and Written Opinion for the International Application No. PCT/NL2022/050211, mailed Jul. 22, 2022, 11 pages.

*Primary Examiner* — Kevin R Steckbauer
(74) *Attorney, Agent, or Firm* — KDW Firm PLLC

(57) ABSTRACT

A method for providing a detection output which is representative for the presence of a molecule of interest in a sample, wherein the method is a computer implemented method including the steps of: providing assay data, wherein said assay data comprises a plurality of data values for a plurality of time points being indicative for at least one detection curve obtained from an assay containing said sample, determining, from said assay data, a value of a second derivative of said detection curve, comparing said determined value of the second derivative with a predetermined non-zero threshold, and providing said detection output if, following from said comparison, said determined value of the second derivative exceeds said threshold.

15 Claims, 5 Drawing Sheets

Figure 1A:
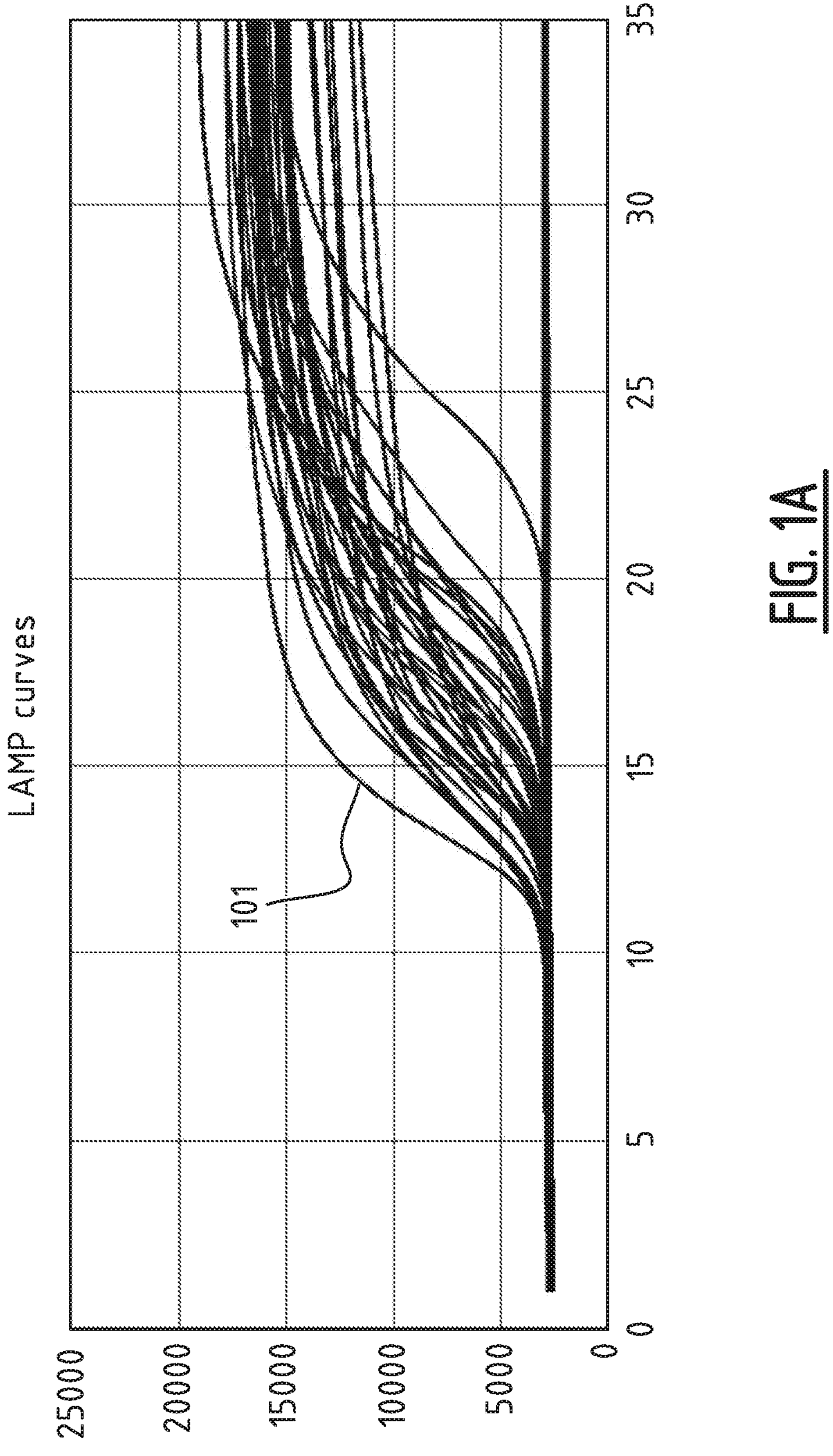

(51) Int. Cl.
*G06V 20/69* (2022.01)
*G16B 25/00* (2019.01)

(56) References Cited

U.S. PATENT DOCUMENTS

| | | | | |
|---|---|---|---|---|
| 7,587,283 | B2 * | 9/2009 | Leong | G16B 40/10 702/19 |
| 8,219,366 | B2 * | 7/2012 | Titz | C12Q 1/6851 703/2 |
| 8,483,972 | B2 * | 7/2013 | Kanderian | G16B 20/20 700/1 |
| 9,607,128 | B2 * | 3/2017 | Kurnik | G16B 40/10 |
| 10,428,375 | B2 * | 10/2019 | Hopper | C12Q 1/6851 |
| 11,360,029 | B2 * | 6/2022 | Hassibi | G01N 21/6454 |
| 11,634,758 | B2 * | 4/2023 | Hopper | C12Q 1/6851 435/6.12 |
| 12,475,973 | B2 * | 11/2025 | Robbins | C12Q 1/686 |
| 2006/0265143 | A1 * | 11/2006 | Taylor, Jr. | G01N 21/5907 702/23 |
| 2008/0154511 | A1 * | 6/2008 | Leong | C12Q 1/6851 702/19 |
| 2008/0154512 | A1 * | 6/2008 | Leong | C12Q 1/6851 435/6.16 |
| 2011/0054852 | A1 * | 3/2011 | Titz | G16B 40/00 703/2 |
| 2012/0116687 | A1 * | 5/2012 | Kanderian | G16B 20/00 702/20 |
| 2014/0377766 | A1 * | 12/2014 | Hopper | G01N 21/6452 435/6.12 |
| 2015/0186598 | A1 * | 7/2015 | Kurnik | C12Q 1/6851 702/104 |
| 2016/0125132 | A1 * | 5/2016 | SantaLucia | G16B 40/30 435/6.12 |
| 2019/0376129 | A1 * | 12/2019 | Hopper | C12Q 1/6851 |
| 2023/0005571 | A1 * | 1/2023 | Robbins | C12Q 1/686 |
| 2024/0290432 | A1 * | 8/2024 | Van 'T Oever | G16B 40/10 |

FOREIGN PATENT DOCUMENTS

| | | | | | |
|---|---|---|---|---|---|
| CN | 114882948 | A | * | 8/2022 | G16B 25/20 |
| CN | 114882948 | B | * | 1/2025 | G16B 40/10 |
| EP | 3231861 | A1 | * | 10/2017 | G01N 21/6452 |
| EP | 3544015 | A1 | * | 9/2019 | G16B 5/00 |
| EP | 3231861 | B1 | * | 1/2020 | C12Q 1/6851 |
| EP | 3090372 | B1 | * | 6/2023 | C12Q 1/686 |
| EP | 3544015 | B1 | * | 10/2024 | G01N 21/6486 |
| JP | 2001314195 | A | * | 11/2001 | G16Z 99/00 |
| JP | 2013503373 | A | * | 1/2013 | G16B 40/10 |
| KR | 20170051539 | A | * | 5/2017 | C12Q 1/686 |
| KR | 20250028452 | A | * | 2/2025 | G01N 21/6428 |
| WO | WO-2008070328 | A2 | * | 6/2008 | C12Q 1/6851 |
| WO | WO-2013113072 | A1 | * | 8/2013 | C12Q 1/6851 |
| WO | WO-2014053467 | A1 | * | 4/2014 | G16B 20/20 |
| WO | WO-2015101591 | A1 | * | 7/2015 | C12Q 1/686 |
| WO | WO-2016052991 | A1 | * | 4/2016 | C12Q 1/686 |
| WO | WO-2022220686 | A1 | * | 10/2022 | C12Q 1/6851 |
| WO | WO-2024238460 | A2 | * | 11/2024 | G16B 40/10 |
| WO | WO-2025080680 | A1 | * | 4/2025 | C12Q 1/6827 |
| WO | WO-2025143555 | A1 | * | 7/2025 | G16B 20/20 |
| WO | WO-2025179343 | A1 | * | 9/2025 | C12Q 1/6851 |

* cited by examiner

METHOD FOR PROVIDING A DETECTION OUPUT WHICH IS REPRESENTATIVE FOR THE PRESENCE OF A MOLECULE OF INTEREST

This application is a national stage filing under 35 U.S.C. 371 of pending International Application No. PCT/NL2022/050211, filed Apr. 16, 2022, which claims priority to Netherlands patent application 2028003, filed Apr. 16, 2021, the entirety of which applications are incorporated by reference herein.

The present invention relates to a method and system for providing a detection output which is representative for the presence of a molecule of interest in a sample.

To determine the presence of a molecule of interest, for instance a virus, a sequence thereof or any other target entity, in a sample, it is known to multiply this target entity to be able detect the presence. Such a process starts with a first molecule that is amplified by enzymes in order to provide a suitable amount to be able to detect the presence. Typical reactions are for example PCR (Polymerase chain reaction) or LAMP (Loop-mediated isothermal amplification). But others are known as well.

It is for instance known to measure the reaction product by labelling the reaction product with fluorescent probes or markers or generally using colour changes, for instance in terms of intensity. By measuring the change in colour over time, a detection curve can be obtained, which is indicative for the strength of the growth or multiplication process, and thus of the presence of the molecule of interest to be detected, over time. Typically, such an assay provides assay data, for instance fluorescence or other color intensity data, wherein said assay data comprises a plurality of data values for a plurality of time points, for instance for a plurality of reaction cycles, being indicative for the detection curve obtained from the amplification-based assay containing the sample.

A peak or plateau in such a detection curve is indicative for the presence of the molecule of interest and such a peak is typically detected using a thresholding technique, wherein a detection output which is representative for the presence of the molecule of interest is output if, and preferably only if, the detection curve or a data value from the plurality of data values in the assay data, exceeds a predetermined threshold.

It is a problem of these known detection methods that the amplification reactions and the respective cycles take time, such that the detection of the presence of the molecule of interest also takes time. Only when sufficient reaction products are amplified, the presence can be detected, i.e. a positive result is obtained. As it is typically not possible to positively detect the absence of the molecule of interest, it is established that the result is negative when, after a predetermined testing time period, the presence if not detected. This testing period is typically determined on the basis of the maximum time of detection of the presence of said molecule of interest in the lowest detectable concentration limit (Limit of Detection or LOD).

It is a goal of the present invention, next to other goals, to provide an improved method for providing a detection output which is representative for the presence of a molecule of interest in a sample, wherein the above mentioned problem is at least partly alleviated.

This goal, amongst other goals, is met by a method according to claim 1. More specifically, this goal, amongst other goals is met by a method for providing a detection output which is representative for the presence of a molecule of interest in a sample, wherein the method comprises the steps of:

- providing assay data, wherein said assay data comprises a plurality of data values for a plurality of time points being indicative for at least one detection curve obtained from an assay containing said sample;
- determining, from said assay data, a value of a second derivative of said detection curve;
- comparing said determined value of the second derivative with a predetermined non-zero threshold, and;
- providing said detection output if, following from said comparison, said determined value of the second derivative exceeds said threshold.

Instead of detecting an absolute threshold of the assay data, i.e. the data values, a value of the second derivative is determined. It was found that comparing the value of this second derivative with a predetermined, non-zero threshold, the presence of the molecule of interest, or any other target entity, can be detected faster. As the presence of the molecule of interest can be detected earlier, also the overall testing time can be shortened, as this testing time is based on the maximum detection time of the presence of the molecule in the lowest detectable concentration (LOD). Further, by comparing the value of the second derivative with a predetermined threshold instead of for instance detecting a peak in the second derivative, the detection process is accelerated.

Next to a decrease in detection time, relying on the second derivative to detect the presence of a molecule of interest form the obtained assay data also makes the detection method less sensitive to absolute values of the assay data, i.e. the data values. As the presence of a molecule of interest is determined on the basis of a change of the change of the assay data, the absolute values of the assay data are less relevant. Variations in baseline that are common in detector systems will not trigger a false result. A more reliable detection process is thus obtained.

Relying on the value of the second derivative as the compared unit has the advantage that the value is available much quicker than other values, such as an end or maximum value of the measurement data. By extension, relying on said comparison, and thus on the value of the second derivative as part of the comparison, for providing the detection output, allows to "call" the end result of the test earlier as well. In particular, in order to establish said result, there is no need to wait once the threshold has been passed by the second derivative value. As such, the maximum detection time for the lowest detectable concentration is reduced, thereby also allowing a quicker negative result.

The comparison may be based on solely the value of the second derivative of the detection curve and the predetermined non-zero threshold.

The assay data preferably contains a plurality of datapoints, for instance data values measured or detected at a plurality of difference points in time. The assay data may thus be considered as coordinate data, wherein each datapoint is representative for a data value at a respective point in time. For determining the value of the second derivative, the detection curve, specifically the data values for the plurality of points of time, can be differentiated twice with respect to time. Preferably, the step of determining the value of the second derivative comprises determining, from said assay data, for at least a period of time a value of a second derivative said detection curve. More generally, a value of a derivative of an order that is higher than one may be determined for comparison.

The step of determining the second derivative may comprise any suitable method for determining the second derivative. The value of the second derivative may for instance be determined, i.e. calculated, for a given data value or for a plurality thereof. Calculating the second derivative for a data value may include calculating said second derivative on the basis of a plurality of data values, preferably including the data value for which the derivative is calculated. Determining the value for the second derivative may for instance include determining a difference over time on the basis of a plurality of data values. Additionally, or alternatively, the second derivative may be determined from differentiating the grow curve as function obtained by a curve fitting method In the step of comparing, the determined value for the second derivative is compared to a threshold. If, and preferably only if, the value of the second derivative exceeds, or is larger than, said threshold, it is determined that the molecule of interest is present. A detection output may then be generated. A detection output is provided if the second derivative exceeds the predetermined threshold, which is representative of the change of the change of the detection curve, as formed by the data values. Such a change may be positive or negative. Preferably, the step of comparing comprises comparing an absolute value of the determined value of the second derivative with a threshold. The detection output may be a signal or may for instance be output in detection output data.

More generally, a method for detecting the presence of a molecule of interest is provided on the basis of assay data, or general sensor data, as mentioned. The method may then comprise the step of establishing the presence, and optionally providing corresponding output, that the presence of the molecule is detected. The method may be computer implemented, for instance executed on a processor in a processing device such as a personal computer, smartphone or dedicated testing system or device. It may also be possible that the method is implemented differently, for instance in a system or device, for instance using analog means for determining, comparing and/or outputting as mentioned.

It is noted that the invention is not limited to a specific assay data or type of assay or detection means used therein. The assay data may for instance be obtained from a PCR or LAMP based assay. The assay data contains data points which may form the detection curve as mentioned. The detection curve may for instance be a growth curve obtained from an amplification-based assay. The assay data may contain fluorescence data, color intensity data or colorimetric data. Other data or means or detecting is however also possible, such as data obtained by electrical or electrochemical detection. Moreover, the detection method may be used to analyze any form of data and to provide a detection output on the basis of the comparison.

Preferably, a plurality of values of the second derivative is determined from the assay data for a grow curve. A change can then be efficiently detected by comparison, thereby accelerating the detection process. The method then preferably also comprises comparing said plurality of determined values of the second derivative with the threshold.

More preferably, for each data value, or at the location of each data value in terms of the coordinate data as mentioned above, a value of the second derivative is determined for comparison. Each data value is thus evaluated, thereby even further accelerating the detection process. As an alternative, for one of a few, for instance two, three, four, five, or six, data values, the value of the second derivative is calculated for comparison. Preferably, when at least one of the determined values of the second derivative exceeds the determined threshold, the detection output is provided.

It is possible that the assay data already comprises a plurality of data values for the complete testing period. A complete amplification process may then be completed, wherein the obtained assay data is subsequently processed to detect any presence. As mentioned, as the new detection method allows accelerated, i.e. earlier, detection of the presence of a molecule of interest, also the complete testing period can be reduced, such that the testing time is reduced.

It is however also possible to detect the presence in real-time during the assay process. According to a preferred embodiment, the step of providing assay data comprises consecutively receiving a plurality of data values, the plurality of data values forming the assay data. The measured data values, for instance fluoresce, intensity or color data, are then processed upon receipt. As mentioned above, preferably for each received data value a second derivative is calculated for comparison. The step of determining the value for the second derivative then preferably comprises calculating, for at least a part, preferably all, of the consecutively received data values, said second derivative based on the assay data. Preferably the method further comprises providing the detection output if, following from said comparison, at least one determined second derivative exceeds said threshold. After the detection of the presence, the process, more preferably also the assay process, may be stopped. This saves time and resources.

According to a further preferred embodiment, the method thus comprises the steps of:

a) providing, or preferably receiving, an data value, said data value being one of a plurality of data values forming the assay data;
b) determining a value of the second derivative for said received data value and on the basis of the assay data;
c) comparing said value of the determined second derivative with the threshold;
d) providing said detection output if, following from said comparison, said determined second derivative exceeds said threshold.

The method then preferably also comprises the steps of repeating steps a-d until said determined second derivative exceeds said threshold. More preferably, the process is stopped after detection of the presence of the molecule of interest in step c.

Typically, the detection curve in general or the data values more specifically may vary over time. To prevent a false positive due to these minor fluctuations over time, it is preferred if the predetermined threshold is determined taking into account any fluctuations of the signal. Thus, according to a preferred embodiment, the method further comprises the step of determining a baseline amount for the second derivative from the plurality of data values, wherein the method further comprises the step of determining the non-zero threshold on the basis of the determined baseline amount. The threshold may be determined to be at least 105%, preferably at least 110%, more preferably at least 120% of said baseline amount.

In terms of efficiency, it is typical that the presence of a molecule of interest, or other target entity, is to be determined for a plurality of samples. As such, the assay data resulting from such an assay may comprise a plurality of channels of data values for a plurality of detection curves representative for a corresponding plurality of samples. The process as described above can be applied separately, for instance in parallel, for each channel in the assay data. A plurality of detection outputs may be generated, or a detection output in the form of detection data may be generated containing data for each of the channels whether a molecule of interest was detected in said channel.

Although it may be possible to detect the presence of the same molecule of interest in a plurality of samples using the multi-channel data as mentioned above, it may also be possible to detect the presence of a plurality of difference molecules of interest in a single sample. Each channel may then be representative of the detection curve of a molecule of interest. At the same time, the presence of a plurality of different molecules of interest may similarly be detected in a plurality of samples.

Although it may be possible to stop the process once for all channels it has been established that the molecule is present in order to shorten the detection process, it is noted also without such interruption the process as a whole is already shortened due to the decrease of the complete testing period as mentioned above, which is based on the maximum detection time.

As such, a method is provided for providing a detection output representative for the presence of a molecule of interest in a plurality of samples, wherein the step of providing optical assay data comprises providing assay data, wherein said assay data comprises a plurality of channels of data values being indicative for a plurality of detection curves obtained from an assay containing said plurality of samples, wherein the steps of determining, comparing and providing any detection output is performed for each, or at least a part, of the plurality of channels.

As discussed above, a value of the second derivative may be determined for comparison for each of the data values in the assay data. This may be done after a complete assay, which may be limited in length in terms of complete testing time or real-time as mentioned above.

Preferably, with reference to steps a)-c) as mentioned above, these steps may be repeated for each of the respective channels in the assay data. For improved resource management, processing of data values in a channel may be stopped after it has been established that the molecule of interest is present in the sample of this channel. As such, the steps a-d may then only be repeated for a respective channel until said determined second derivative exceeds said threshold in said respective channel. The determination of the second derivative and/or the comparison may thus be stopped for a channel for the presence has been established.

According to a further aspect, a computer program product is provided comprising a computer-executable program of instructions for performing, when executed on a computer, the steps of the above mentioned method.

According to a further aspect a system is provided for providing a detection output which is representative for the presence of a molecule of interest in a sample, comprising:

- an input for receiving assay data, wherein said optical assay data comprises a plurality of data values being indicative for at least one detection curve obtained from an assay containing said sample;
- an output for providing said detection output, and;
- a processing unit arranged to perform the method as described above.

Figure 1B:
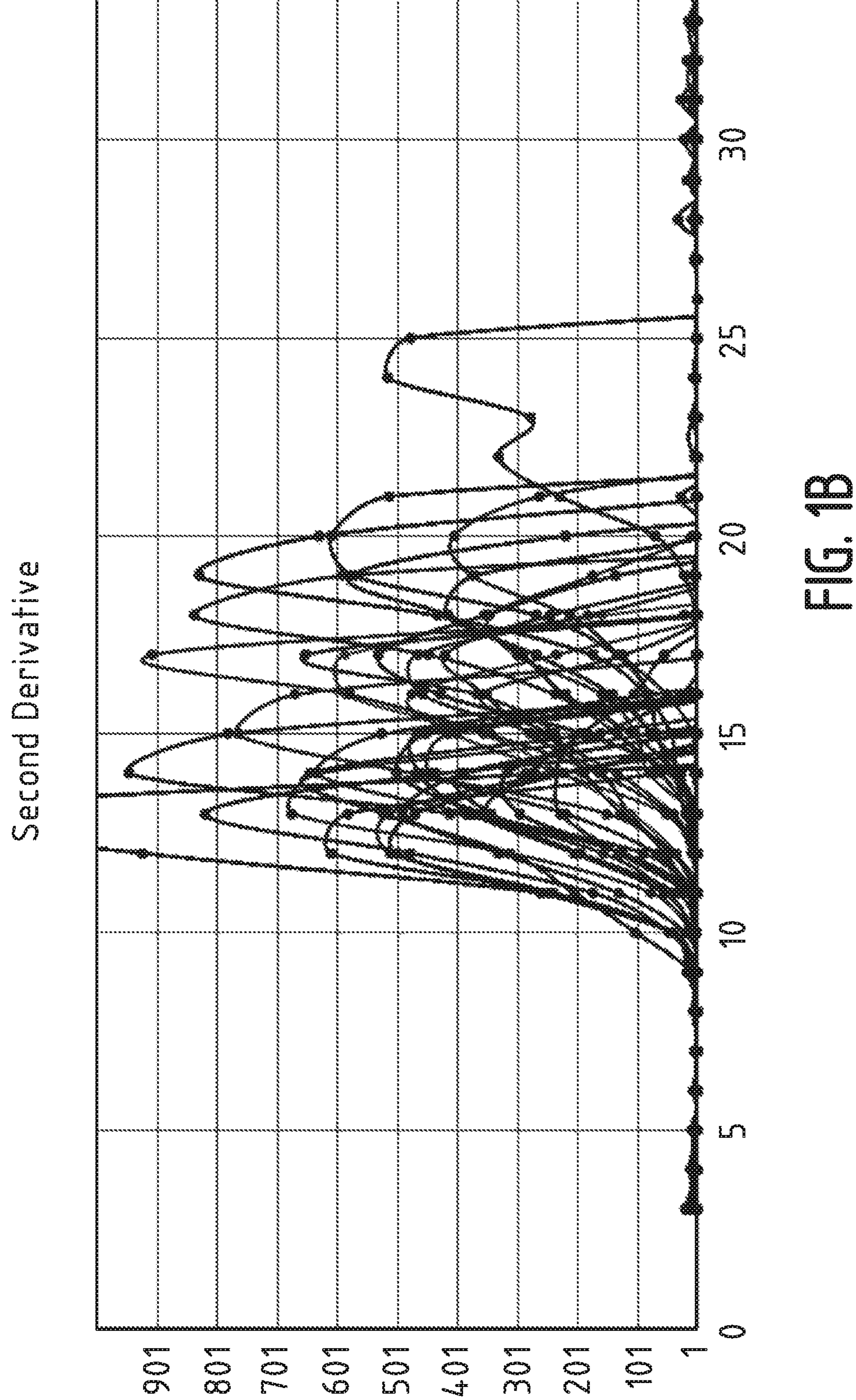
Figure 2:
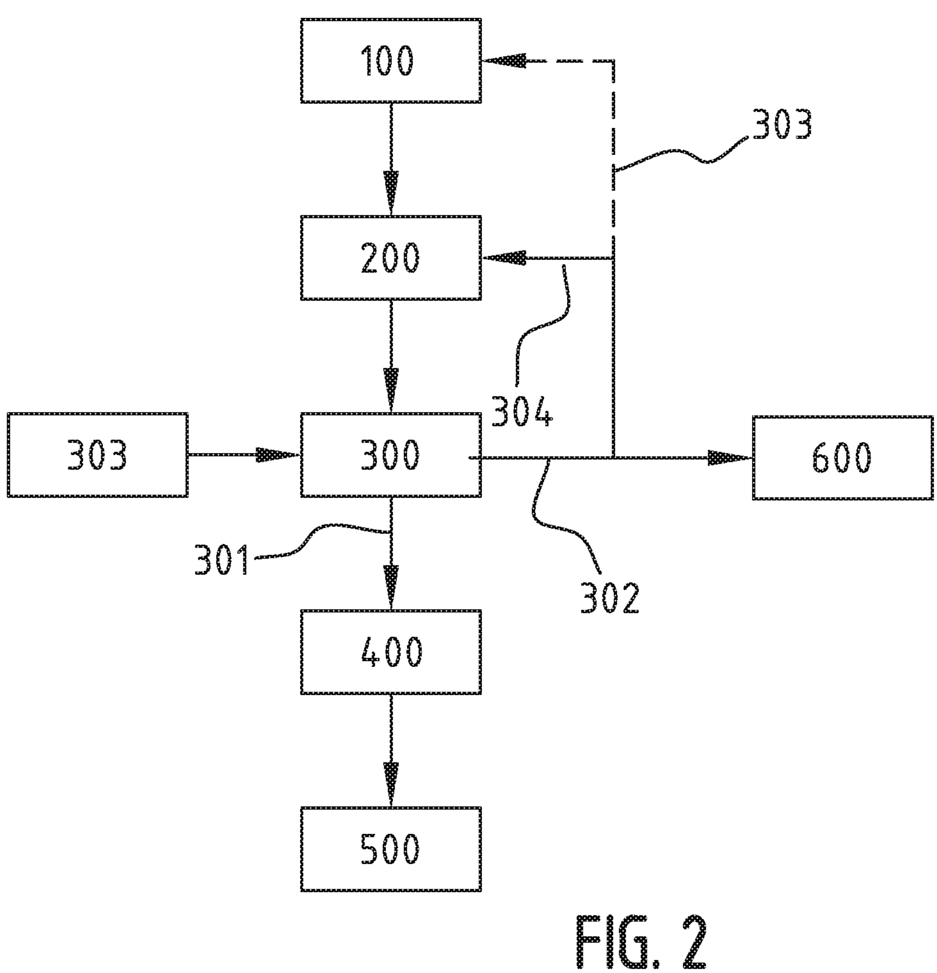
Figure 3:
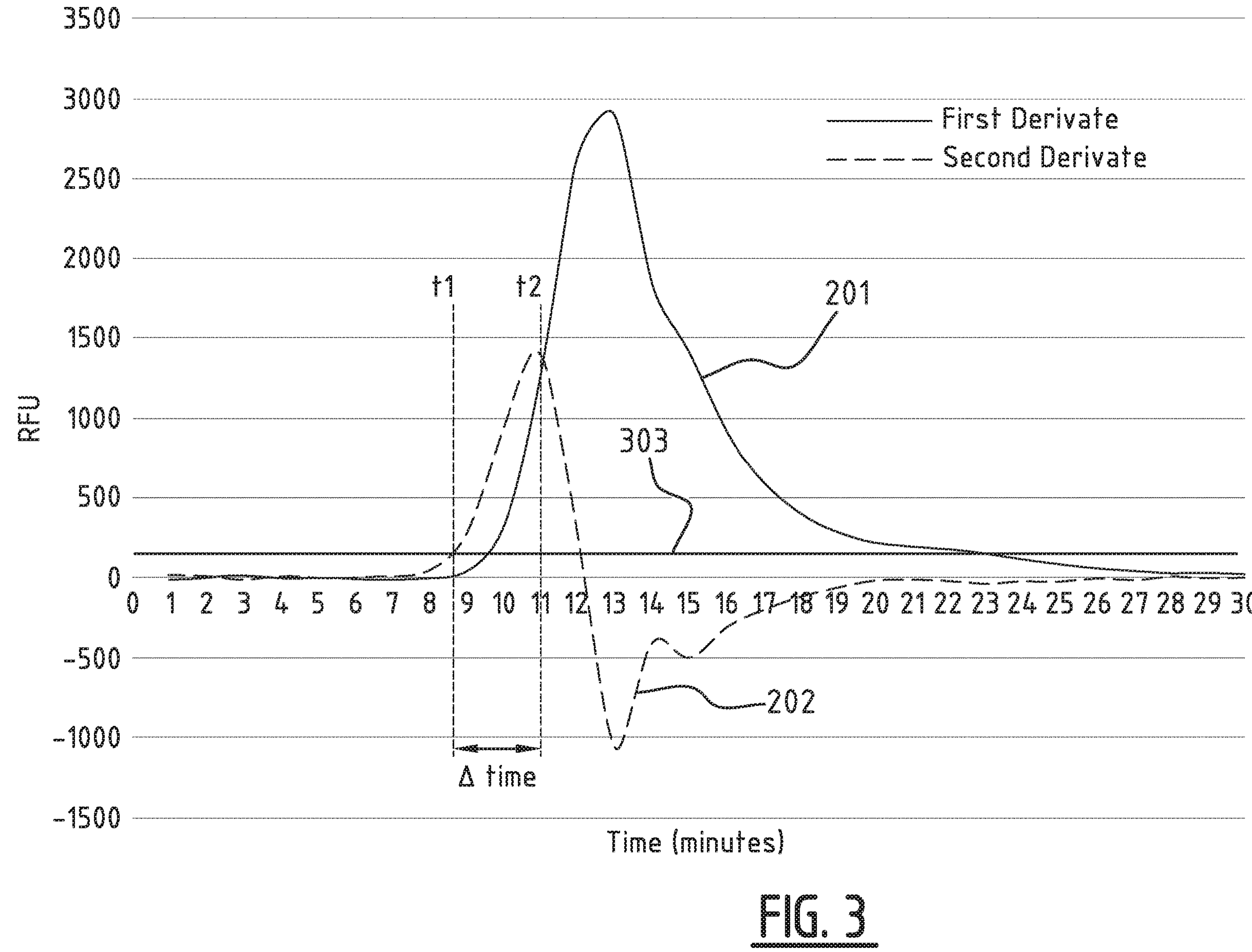
Figure 4:
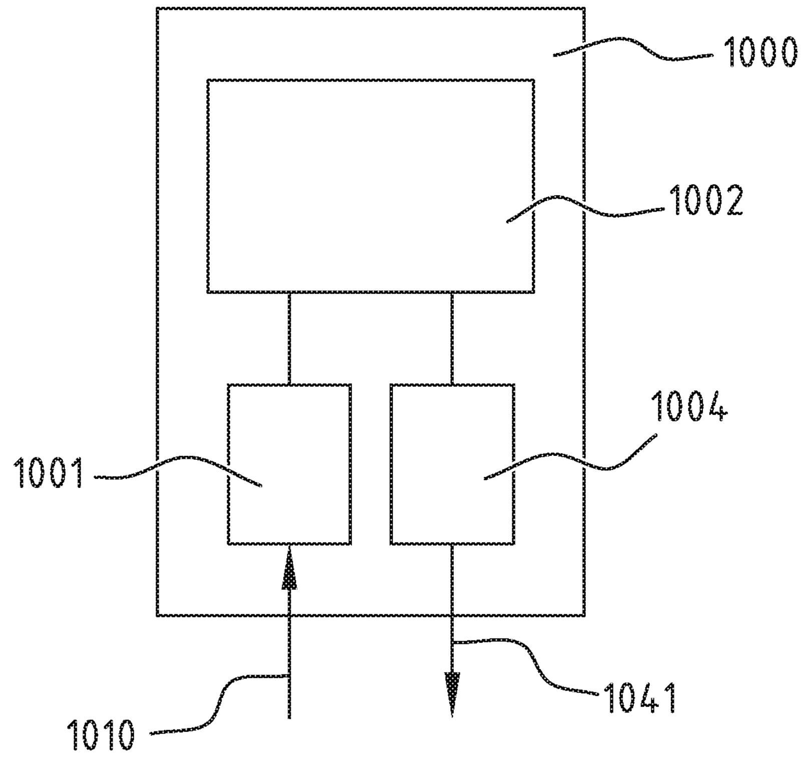

The present invention is further illustrated by the following Figures and example, which show a preferred embodiment of the method according to the invention, and are not intended to limit the scope of the invention in any way, wherein:

FIGS. 1*a* and 1*b* show assay data comprising a plurality of channels obtained from an assay for a plurality of samples and the second derivatives of the channels, respectively;

FIG. 2 schematically shows an embodiment of the detection method;

FIG. 3 shows the first and second derivatives of a detection curve, and;

FIG. 4 schematically shows an embodiment of a detection system.

In FIG. 1*a*, an example of assay data (indicated with reference numeral 1010 in FIG. 4) is shown comprising a plurality of channels which each comprise a plurality of data values over time defining a plurality of detection curves. In this example, the assay data is obtained from a LAMP based assay for determining the presence of a molecule of interest in a plurality of samples. It can be seen that at different points, some of the detection curves start to show exponential behavior. One of these curves is indicated with reference numeral 101. Typically, this is indicative for the presence of a molecule of interest in the sample from which the detection curve is obtained.

To provide a detection output 1041 (see FIG. 4) which indicates that a molecule of interest is present in a sample, a detection method is provided which is schematically shown in FIG. 2. A suitable system 1000 for detecting this presence is shown in FIG. 4. In a first step 100 (FIG. 2), assay data 1010 is obtained, for instance using a suitable input 1001 (FIG. 4). The assay data 1010 may be a complete data set as shown in FIG. 1*a*. It may also comprise partial data to which data points are added when they become available from the assay during analysis. The system 1000 comprises a processor 1002 for analyzing the data.

As a second step 200, a value for the second derivative 202 (see FIGS. 1*b* and 3) is determined. It may be the case that the second derivative is determined for each of the data points, or at least a plurality thereof, from a complete data set, which is plotted in FIGS. 1*b* and 1*n* FIG. 3 together with the first derivative 201. The determined second derivative may then be a data set. In the alternative, a value for the second derivative is determined for each data point on receipt, for instance while the data is fed from the assay during analysis.

In the next step 300, the determined value of the second derivative 202, or the plurality thereof, is compared to a predetermined non-zero threshold 303, see also FIG. 3. If, and preferably only if, the determined second derivative, or at least one of the determined values, exceeds the threshold, the method moves to step 400 (indicated with arrow 301). In step 400, a detection output 1041 (see FIG. 4) is provided which indicates that the presence of the molecule is detected. Typically, the detection output is a (digital) signal or data file indicating the presence. The step 400 can thus be considered as establishing that the sample contained the molecule of interest.

If it on the other hand follows from the comparison 300 that the threshold 303 is not exceeded, the process may move the step 600. In particular when the complete data set is analyzed as a whole, wherein the second derivative is a data set comprising a plurality of values and wherein it is determined that none of the values for the second derivative exceeds the threshold, it is established that the presence of the molecule is not detected. A corresponding output, for instance a negative output, may thus be provided, also using the output 1004 for instance. The method may then stop.

It may also be the case that the analysis of data is performed per data point, for instance upon receipt of each data point. In that case, if it is determined that the determined second derivative does not exceed the threshold, the process may move back to step 100 (arrow 303) to receive a next data point, or a plurality thereof, for further processing according to steps 200 and 300. In this iterative process, the process may be stopped (step 500) after establishing the presence. Step 500 may occur prior to or at the same time as step 400.

It may also be the case that a compete data set is analyzed iteratively, i.e. per data point or sets of data points. When the threshold is then not exceeded, the process may move from step 300 via arrow 304 back to step 200 to determine a new value of the second derivative, or a plurality thereof, for further comparison in step 400.

It is preferred if the process as described is performed for the plurality of channels. This may take place in parallel, i.e. upon receipt of a data point for a channel. The process, preferably via arrow 303 if applicable, is performed for the respective data point for the respective channel. A next process may then be started for a next channel. Step 100 may also include receiving data points from a plurality of channels and comparing the respective second derivatives to the thresholds.

It will be appreciated that by basing the detection on the second derivative, and in particular by comparison to a threshold, the detection takes place faster. For instance when comparing the detection to a process wherein the presence would be established by determining a peak in the second derivative, indicated with the dashed line at t2 in FIG. 3, a reduction of the time of an assay by approximately 10-20% can be achieved, see the point t1 indicating the point of detection according to the process as described.

In the table below, a comparison is made between the minimal, average and maximum time (data points) of the assay to accurately assess the presence of a molecule of interest, based on a data file obtained from a LAMP assay. The data file comprises 46 datapoints for a plurality of channels. In method 1 as mentioned below, a sample is assumed to be a positive when the detection curve, i.e. the data points, exceeds a predetermined threshold, in this example 4000 RFU. In method 2, a sample is determined to be a positive when a maximum is detected in the second derivative (see point t2 in FIG. 3). Method 3 relies on a detection using a predetermined threshold, in this example 40 RFU, on the second derivative:

| | Cut of | | Time of assay | | |
|---|---|---|---|---|---|
| | time | Threshold | Min | Average | Max |
| Method 1 | 30 min | 4000 | 1 | 12.3 | 22 |
| Method 2 | | | 12 | 14.2 | 41 |
| Method 3 | 30 min | 40 | 9 | 10.5 | 19 |
| Difference in time to positive | | | −8 | 1.8 | 3 |

It will be appreciated that with the method employing thresholding of the second derivative (method 3), the presence is detected at datapoint 19 at latest, compared to for instance datapoint 22 in the normal thresholding (method 1) and datapoint 41 for method 2. A time reduction is thus achieved, without any false negatives.

The functions of the various elements shown in the figures, including any functional blocks labelled as "processors", may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor (DSP) hardware, network processor, application specific integrated circuit (ASIC), field programmable gate array (FPGA), read only memory (ROM) for storing software, random access memory (RAM), and non volatile storage. Other hardware, conventional and/or custom, may also be included. Similarly, any switches shown in the figures are conceptual only. Their function may be carried out through the operation of program logic, through dedicated logic, through the interaction of program control and dedicated logic, or even manually, the particular technique being selectable by the implementer as more specifically understood from the context.

It should be appreciated by those skilled in the art that any block diagrams herein represent conceptual views of illustrative circuitry embodying the principles of the present invention. Similarly, it will be appreciated that any flowcharts, flow diagrams, state transition diagrams, pseudo code, and the like represent various processes which may be substantially represented in computer readable medium and so executed by a computer.

Whilst the principles of the present invention have been set out above in connection with specific embodiments, it is to be understood that this description is merely made by way of example and not as a limitation of the scope of protection which is determined by the appended claims.

The invention claimed is:

1. A computer-implemented method for providing a detection output which is representative for the presence of a molecule of interest in a sample, the method being performed by a detection system, comprising the steps of:
- providing assay data, wherein said assay data comprises a plurality of data values for a plurality of time points being indicative for at least one detection curve obtained from an assay containing said sample;
- determining, from said assay data, a value of a second derivative of said detection curve;
- comparing said determined value of the second derivative with a predetermined non-zero threshold, and;
- providing said detection output in response to determining that an absolute value of said determined value of the second derivative exceeds said threshold, wherein said providing of the detection output enables faster detection of the presence of the molecule of interest relative to detection based on the detection curve without the use of said comparison of said second derivative and said threshold.

2. The method according to claim 1, comprising determining a plurality of values of the second derivative from the assay data and comparing said plurality of determined values of the second derivative with the threshold.

3. The method according to claim 2, comprising determining a value for the second derivative from the assay data for each data value.

4. The method according to claim 1, wherein the step of providing assay data comprises consecutively receiving a plurality of data values, the plurality of data values forming the assay data, wherein the step of determining the value for the second derivative comprises calculating, for at least a part of the consecutively received data values, said second derivative based on the assay data, wherein, if following from said comparison, at least one determined second derivative exceeds said threshold, the detection output is provided.

5. The method according to claim 1, comprising the steps of:

a) receiving a data value, said data value being one of a plurality of data values forming the assay data;

b) determining a value of the second derivative for said received data value and on the basis of the assay data;

c) comparing said value of the determined second derivative with the threshold;

d) providing said detection output if, following from said comparison, said determined second derivative exceeds said threshold.

6. The method according to claim 5, further comprising:

e) repeating steps a-d until said determined second derivative exceeds said threshold as determined in step d.

7. The method according to claim 1, further comprising the step of determining a baseline amount for the second derivative from the plurality of data values, wherein the method further comprises the step of determining the non-zero threshold on the basis of the determined baseline amount, wherein said threshold is determined to be at least 105% of said baseline amount.

8. The method according to claim 1, wherein the method is performed for a plurality of samples, wherein the step of providing assay data comprises providing assay data comprises a plurality of channels of data values being indicative for a plurality of detection curves obtained from an assay containing said plurality of samples, and wherein the steps of determining, comparing and providing any detection output is performed for each of the plurality of channels.

9. The method according to claim 5, wherein the step of providing assay data comprises providing assay data comprises a plurality of channels of data values being indicative for a plurality of detection curves obtained from an assay containing said plurality of samples, and wherein steps a-d are repeated for each of the respective channels in the optical assay data.

10. The method according to claim 6, wherein steps a-d are repeated for each of the respective channels in the optical assay data, and wherein steps a-d are only repeated for a respective channel until said determined second derivative exceeds said threshold in said respective channel.

11. A computer-readable storage medium comprising instructions that, when executed on a computer, cause the computer to perform the steps of the method of claim 1.

12. A system for providing a detection output which is representative for the presence of a molecule of interest in a sample, comprising:

a processing unit arranged to perform the method according to claim 1.

13. The system according to claim 12, wherein the output is arranged to provide an output datafile.

14. The method according to claim 7, wherein said threshold is determined to be at least 110% of said baseline amount.

15. The method according to claim 7, wherein said threshold is determined to be at least 120% of said baseline amount.

* * * * *